United States Patent [19]

Creighton et al.

[11] Patent Number: 5,278,187
[45] Date of Patent: Jan. 11, 1994

[54] PHARMACEUTICAL COMPOSITIONS

[75] Inventors: Andrew M. Creighton, London; William A. Jeffery, Maldon, both of England

[73] Assignee: British Technology Group Ltd., London, England

[21] Appl. No.: 764,822

[22] Filed: Sep. 24, 1991

Related U.S. Application Data

[62] Division of Ser. No. 597,180, Oct. 17, 1990, Pat. No. 5,149,710, which is a division of Ser. No. 422,673, Oct. 17, 1989, abandoned, which is a division of Ser. No. 183,067, Apr. 19, 1988, Pat. No. 4,902,714, which is a division of Ser. No. 842,857, Mar. 24, 1986, Pat. No. 4,755,619.

[30] Foreign Application Priority Data

Apr. 1, 1985 [GB] United Kingdom ............... 8508508

[51] Int. Cl.$^5$ .................. A61K 31/35; A61K 31/36; A61K 31/275; A61K 31/215; A61K 31/225; A61K 31/235
[52] U.S. Cl. ..................... 514/459; 514/466; 514/519; 514/521; 514/528; 514/529; 514/533; 514/547; 514/548
[58] Field of Search ............... 514/459, 466, 514, 521, 514/528, 529, 533, 547, 548

[56] References Cited

U.S. PATENT DOCUMENTS

| | | | |
|---|---|---|---|
| 3,164,580 | 1/1965 | Matson | 560/169 |
| 3,351,658 | 11/1967 | Bersworth | 560/169 |
| 3,497,535 | 2/1970 | Lennon | 560/169 |
| 3,941,790 | 3/1976 | Creighton | 560/169 |
| 4,275,063 | 6/1981 | Creighton | 560/169 |
| 4,432,907 | 2/1984 | Wieder | 560/169 |

FOREIGN PATENT DOCUMENTS 1234935 6/1971 United Kingdom .
1374979 11/1974 United Kingdom .

OTHER PUBLICATIONS

Creighton, Chem. Abstract 93:197550 d(1980).
Sinkula, et al., Jour. of Pharmaceutical Sc. 1875 vol. 64, pp. 181–210.
Zhang et al., Acta Pharmaceutical Sinica 1980 vol. 15, pp. 557–583.
Ren et al., Abs of Papers of the Amer. Chem. Soc. Aug. 1981 vol. 182 No. 18.

(List continued on next page.)

Primary Examiner—Jerome D. Goldberg
Attorney, Agent, or Firm—Nixon & Vanderhye

[57] ABSTRACT

Compounds of formula (II)

$$R_3O.CO.CH_2 \diagdown \diagup CH_2.CO.OR_3$$
$$N-CHR_1-CHR_2-N$$
$$NH_2.CO.CH_2 \diagup \diagdown CH_2.CO.NH_2$$
(II)

wherein $R_1$ and $R_2$ are each separately selected from hydrogen, alkyl, alkenyl and alkynyl groups having up to a maximum of four carbon atoms and being unsubstituted, and alkyl, alkenyl and alkynyl groups having up to a maximum of three carbon atoms and being substituted by one, or in the case of fluoro by one or more, substituents but with the proviso that when $R_1$ is hydrogen then $R_2$ is hydrogen or methyl, or $R_1$ and $R_2$ together constitute an ethylene bridging group, and $R_3$ is a group which under physiological conditions undergoes elimination with the formation of a 3,5-dioxopiperazinyl ring, with the further proviso that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, are of value as prodrugs, particularly for effecting cardioprotection.

28 Claims, 1 Drawing Sheet

OTHER PUBLICATIONS

Figure 1:
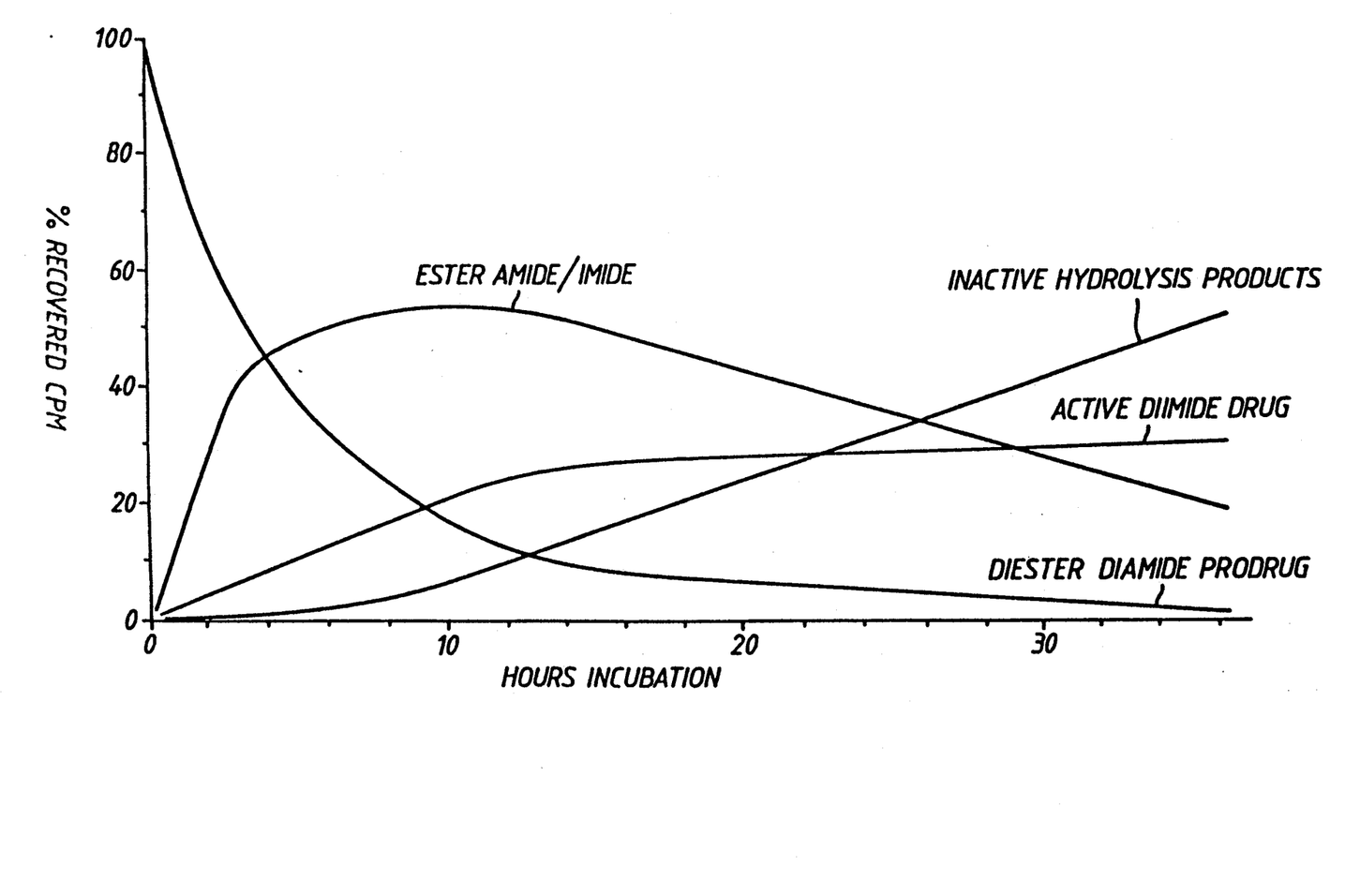

Houghton et al., Jour. of the Chem. Soc. Perkins Transactions I, 1982, pp. 2693–2696.

Creighton et al. Scientific Report of the Imperial Cancer Research Fund for 1983–1984, Apr. 2, 1985.

Herman et al. "Biological Properties of ICRF-159 . . . " Advances in Pharmacology & Chemotherapy, vol. 19, pp. 249–291 (1982).

Herman et al. "Composition of the Effectiveness . . . " Cancer Research 45, 276–281, Jan. 1985.

Von Hoff et al. "Phase 1 Study of ICRF-187 . . . " Cancer Treatment Reports vol. 65, No. 3–4 Mar.–Apr. 1981.

Cal et al. "MST-16 ASB-21, New Antitumor Agents" Poster Session 14th Internl Congress of Chemotherapy, Jun. 23–18 1985, Japan, pp. 1–9.

Creighton et al. "Ester Amide Derivatives of . . . " Recent Advances in Chem., Proc. of the 14th Intl Cong. of Chem. Japan 1985 481–482.

Herman et al. "Comparison of the Protective Effect . . . " Res. Comm. in Chemical Path. & Pharma. vol. 48, No. 1 Apr. 1985, pp. 39–55.

May et al. "Metal Binding by Pharmaceuticals . . . " Agents and Actions, vol. 15, 3/4 (1984), pp. 448–453.

Creighton et al. "Ester Amide Derivatives . . . " 14th Intl Cong. of Chemotherapy, Abstract Form.

PHARMACEUTICAL COMPOSITIONS

This is a division of application Ser. No. 07/597,180, filed Oct. 17, 1990 now U.S. Pat No. 5,149,710, which is a division of 07/422,673 filed Oct. 17, 1989, now abandoned, which is a division of 07/183,067 filed Apr. 19, 1988, now U.S. Pat. No. 4,902,714, which is a division of 06/842,857 filed Mar. 24, 1986, now U.S. Pat. No. 4,755,619.

This invention relates to pharmaceutical compounds and to compositions containing them, being primarily concerned with substances of use in the therapy of certain non-malignant forms of proliferative disease such as psoriasis, and of certain inflammatory conditions such as uveitis.

In UK Patents Nos. 1,234,935 and 1,374,979 certain pharmaceutical compositions have been described having activity of the above type. These compositions contain as active components compounds of formula (I) wherein $R_1$ and $R_2$ are each separately selected from hydrogen, unsubstituted alkyl, alkenyl and alkynyl groups having a chain with up to a maximum of four carbon atoms and substituted alkyl, alkenyl and alkynyl groups having a chain with up to a maximum of three carbon atoms and being limited, except in the case of fluoro, to containing one substituent only but with the proviso that when $R_1$ is hydrogen then $R_2$ is hydrogen or methyl, or $R_1$ and $R_2$ together constitute an ethylene bridging group. Although these compounds, particularly that having $R_1=H$ and $R_2=CH_3$, have proved to be of value in the treatment of both cancer and psoriasis, it is clear that their original promise has not been fully realised. It has now been found, however, that the administration of the compounds in a particular prodrug form offers the potential for overcoming the limitations upon their value arising from the use of the compounds (I) as such.

Accordingly the present invention comprises a compound of formula (II)

wherein $R_1$ and $R_2$ are each separately selected from hydrogen, alkyl, alkenyl and alkynyl groups having up to a maximum of four carbon atoms and being unsubstituted, and alkyl, alkenyl and alkynyl groups having up to a maximum of three carbon atoms and being substituted by one, or in the case of fluoro by one or more, substituents but with the proviso that when $R_1$ is hydrogen then $R_2$ is hydrogen or methyl, or $R_1$ and $R_2$ together constitute an ethylene bridging groups, and $R_3$ is a group which under physiological conditions undergoes elimination with the formation of a 3,5-dioxopiperazinyl ring, with the further proviso that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, for use in therapy.

It has been found that the prodrug compounds (II) do not undergo simple hydrolysis of the two similar ester groups in vivo which would result in a non-cyclic diamide diacid compound of formula (II) as described hereinafter but instead eliminate two $R_3OH$ molecules with the formation of the two rings as desired. By modification of the nature of the ester groups it is possible to alter the water solubility, lipophilicity and rate of conversion to the active cytotoxic molecules (I). For example the methyl, lower hydroxyalkyl and lower alkoxyalkyl esters have much greater water solubilities than the cyclic diimides which they generate, for example the diimide (I) in which $R_1=R_2=H$, has a water solubility of about 0.01 w/v at 20° C. and pH 7.2 and is therefore difficult to use parenterally whilst also not being well absorbed by mouth, whereas the corresponding esters in which $R_3=CH_3$ or $CH_2CH_2OH$ have water solubilities of >2% w/v and can readily be used for parenteral administration. Similarly, increased lipophilicity may be obtained in these prodrugs by the introduction of, for example, hydrocarbon groupings such as isobutyl or benzyl and this is reflected by the relatively high Rf values in a 50% v/v chloroform/ethanol/$SiO_2$ thin layer chromatography system as recorded in the Examples given hereinafter. An increased lipophilicity favours better absorption and changes in tissue distribution such as greater penetration of the central nervous system. The more lipophilic products are also the most attractive candidates for the percutaneous treatment of psoriasis. Further, depending upon whether $R_3$ is an electron-withdrawing group, for example benzyl, propargyl or carbethoxymethyl, or an electron-repelling group, for example isobutyl, hydroxyethyl or methoxyethyl, the rate of conversion of the compound (II) to the corresponding compound (I) can be speeded up or slowed down. Thus, by providing some control over the water solubility, lipophilicity and rate of generation of the active species, the prodrug compounds of the present invention provide the ability to modify the tissue distribution and pharmacodynamics of the dioxopiperazine drugs with consequential therapeutic benefit to the patient.

The group $R_3$ is eliminated under physiological conditions and, although it is possible that enzymic catalysis may be involved in some cases, the elimination will usually occur spontaneously and may be tested for in vitro by incubation of the compound (II) under physiological conditions (i.e. pH 7.2, 37° C.), for example as described in Example 11(B). Whilst a very wide range of alkyl, alkenyl and alkynyl groups having a maximum of up to ten carbon atoms and being unsubstituted or substituted may be used as the group $R_3$, it has been found that certain groups $R_3$ such as t-butyl groups normally undergo $S_N1$ reactions which do not involve cyclisation so that no significant amount of the desired compound (I) is produced. For this reason, the unsubstituted and substituted alkyl, alkenyl and alkynyl groups $R_3$ of use in the present invention preferably contains a bonding carbon atom, i.e. that atom linked to the group which carries at least one hydrogen atom. Subject to this preference, $R_3$ may conveniently be selected from alkyl, alkenyl and alkynyl groups having up to a maximum of ten carbon atoms which may be either unsubstituted or substituted. Preferred groups $R_3$ are such unsubstituted alkyl, alkenyl and alkynyl groups and aralkyl, aralkenyl and aralkynyl groups in which the aromatic part of the group may optionally be substituted by one or two substituents selected from halogen, lower alkyl, lower alkoxy (including a single methylenedioxy), amino and nitro groups and the aliphatic part of the group, which is of a similar size to the unsubstituted aliphatic groups, may optionally be substituted by one substituent selected from alkoxycarbonyl and cyano. Another preferred form for $R_3$ is alkyl, alkenyl and alkynyl groups which have a maximum of up to ten carbon atoms and which are substituted by one or more halogeno (for example fluoro, chloro or bromo), hydroxy, alkoxycarbonyl, benzyloxycarbonyl, cyano, amino (and mono and dialkylamino) groups, or alternatively alkoxy or carboxy groups. Among these, the substituted alkyl groups, especially the alkoxyalkyl groups which may conveniently contain up to a maximum of ten carbon atoms in total, are of particular interest. Another form of substituted alkyl, alkenyl and alkynyl group which is preferred is that containing an oxo substituent, for example the oxo-alkyl groups acetonyl and phenacyl, such groups providing ketonic esters, particularly $\beta$-keto esters.

Among the various alkyl, alkenyl and alkynyl groups $R_3$, both unsubstituted and substituted, it is preferred for reasons of ease of synthesis and stability of the compound (II) prior to administration that the bonding carbon atom of the group, as defined hereinbefore, is not linked to any atom which is not hydrogen or carbon and, moreover, conveniently also is not unsaturated, i.e. is not linked to any adjacent atom by a double or particularly a triple bond. Moreover, while the groups, for example alkyl groups, may be substituted by one or more substituents, groups containing one or two substituents are preferred, and conveniently only one substituent in most cases although with some substituent groups, such as alkoxycarbonyl groups, the presence of two substituents may be of value. Those comments also apply to aralkyl, aralkenyl and aralkynyl groups which most usually contain two or particularly one aryl group, although groups such as the diphenylmethyl group may be of interest in resisting the esterase activity which occurs in some animal species as discussed hereinafter. As regards the aromatic groups, the preferred form of group is an unsubstituted or substituted naphthyl or particularly phenyl group.

It should be appreciated that the terms alkyl, alkenyl and alkynyl are used throughout this specification to include both straight and branched groups. Alkyl, alkenyl and alkynyl groups $R_3$ of one to four carbon atoms in the case of alkyl groups and two to four carbon atoms in the case of alkenyl and alkynyl groups are of most interest, whether unsubstituted or substituted. The terms lower alkyl and lower alkoxy are used in the discussion of the substituent groups in $R_3$ to indicate a group of one to four carbon atoms and in those cases where the term alkyl or alkoxy is used without qualification the preference is for groups of one to ten carbon atoms, particularly of one to four carbon atoms.

Preferred groups $R_3$ are unsubstituted alkyl, alkenyl and alkynyl groups and substituted alkyl groups (including aralkyl groups). Specific examples of preferred groups $R_3$ are as follows (the terms ethyl, propyl and butyl used without qualification in the names of the substituted groups as usual indicate a substituted n-alkyl group (and similarly for alkoxy groups present as a substituent) but, except where indicated, without any restriction upon the position of the substituent in the carbon chain of that alkyl group although, as mentioned hereinbefore, substitution upon the bonding carbon atom is generally of lesser interest, substitution upon the terminal carbon of the chain usually being of most interest; in the cases where $R_3$ is a substituted benzyl group, substitution at the $\alpha$-position is specifically indicated and where this is not done the substituent is located on the ring): methyl, ethyl, n-propyl, n-butyl, isobutyl, allyl, propargyl, benzyl, $\alpha$-methylbenzyl, $\alpha$-ethoxycarbonylbenzyl (i.e. $\alpha$-carbethoxybenzyl), nitrobenzyl, aminobenzyl, mono and dichlorobenzyl, chloro-3,4-methylenedioxybenzyl (i.e. chloropiperonyl), mono and dimethoxybenzyl, mono and dimethylbenzyl, cinnamyl, methoxyethyl, ethoxyethyl, propoxyethyl, butoxyethyl, hydroxyethyl, hydroxypropyl, hydroxybutyl, ethoxycarbonyl methyl (i.e. carbethoxymethyl), ethoxycarbonylethyl, ethoxycarbonylpropyl, carboxymethyl, carboxyethyl, carboxypropyl, benzyloxycarbonylmethyl, benzyloxycarbonylethyl, benzyloxycarbonylpropyl, t-butoxycarbonylmethyl, t-butoxycarbonylethyl, t-butoxycarbonylpropyl, diethoxycarbonylmethyl, cyanomethyl, acetonyl, phenacyl, and 3-dimethylaminopropyl, the alkyl groups preferably being terminally substituted where more than one possibility exists. Specific groups $R_3$ are further illustrated by those present in the compounds of the Examples.

Preferably the carbon chain of the groups $R_1$ and $R_2$, which may be straight or branched, contains from one to three carbon atoms in the case of alkyl groups and two to three carbon atoms in the case of alkenyl and alkynyl groups. More conveniently, when the groups are substituted, particularly by substituent groups other than fluoro, they contain one or two carbon atoms in the case of alkyl groups and two carbon atoms in the case of alkenyl and alkynyl groups. Although substituted groups $R_1$ and $R_2$ are in general of rather lesser interest, some substituted alkyl, and also alkenyl and alkynyl groups, do however possess certain advantages, for example enhanced solubility of the active compound (I), but this is of lesser importance when a prodrug form of the compound is administered. The various substituents which may be present include phenyl, carboxy and alkoxycarbonyl (i.e. carbalkoxy) groups but more particularly halogeno, hydroxy and alkoxy groups. It is preferred that the size of the groups $R_1$ and $R_2$ is not too great since this tends to lead to a reduction in activity, and for this reason compounds in which the substituent group is located at the terminal carbon atom of the chain are preferred. In general those compounds in which both $R_1$ and $R_2$ are relatively large substituted groups are of less interest, those in which only one of $R_1$ and $R_2$ is substituted being of more interest. Conveniently the substituted groups are limited to those having a steric effect in the molecule not substantially greater than that of an isopropyl group. Thus, preferred substituents are fluoro, hydroxy and methoxy, but also chloro and additionally ethoxy, carboxy and methoxycarbonyl. For similar reasons it is preferred that the number of fluoro atoms in any substituted group is limited to five and conveniently to three. Moreover, particularly in the case of substituents such as phenyl, ethoxy, carboxy and methoxycarbonyl, but also with other substituents, substituted ethyl, and particularly substituted methyl groups are of especial interest.

Examples of specific substituted groups $R_1$ and $R_2$ are the substituted saturated groups chloromethyl, pentafluoroethyl, and particularly hydroxymethyl, 2-hydroxyethyl, methoxymethyl, trifluoromethyl and 2,2,2-trifluoroethyl. However, as indicated hereinbefore the unsubstituted groups $R_1$ and $R_2$ are of greater interest, preferred compounds (II) being those in which both $R_1$ and $R_2$ are hydrogen, or $R_1$ is methyl and $R_2$ is hydrogen, methyl, ethyl, n-propyl, isopropyl, allyl or propargyl, or $R_1$ and $R_2$, which are different or preferably the same, are both selected from ethyl, n-propyl, isopropyl, allyl and propargyl, or $R_1$ and $R_2$ together represent an ethylene bridging group.

Particularly preferred are those compounds where both $R_1$ and $R_2$ are hydrogen or $R_1$ is methyl and $R_2$ is methyl, ethyl or especially hydrogen, or both $R_1$ and $R_2$ are ethyl, whilst $R_3$ is selected from methyl, ethyl, isobutyl, allyl, propargyl, benzyl, α-methylbenzyl, α-carbethoxybenzyl, o-nitrobenzyl, aminobenzyl, 2,6-dichlorobenzyl, methoxyethyl, ethoxyethyl, propoxyethyl, butoxyethyl, hydroxyethyl, hydroxypropyl, hydroxybutyl, ethoxycarbonylmethyl, diethoxycarbonylmethyl, benzyloxycarbonylmethyl, ethoxycarbonylpropyl, carboxymethyl and acetonyl.

As indicated hereinbefore, when neither $R_1$ nor $R_2$ is hydrogen, the compounds (II), like the compounds (I), are limited to those in which the groups $R_1$ and $R_2$ are adjacently disposed in the meso or erythro configuration rather than oppositely disposed in the dl or threo, configuration except that in the particular case when $R_1$ and $R_2$ together constitute an ethylene bridging group the configuration of the resultant cyclobutane ring may be cis or trans. However, when $R_1$ and $R_2$ are not identical the compounds can exist in two enantiomorphic forms, the invention including the use of the various different isomers of such compounds. In some cases the optically active d- and l-isomers may have the advantage of significantly higher water solubility than the corresponding dl-racemate and it may also be the case that the biological activity of the compound will differ as between the isomers. The invention does therefore extend to the use of such compounds in a form in which the amount of the compound in the d or l configuration is greater than that in the l or d configuration. In particular the compound may be essentially in the form of the d or l isomer, for example being substantially free (i.e. containing no more than 10%) from the dl and l or dl and d isomers.

The preparation of the simplest compound (II) of use in the present invention ($R_1=R_2=H$ and $R_3=CH_3$) has been described by Houghton and Williams (Journal of the Chemical Society, Perkin Transactions I, 1982, 2693) in a paper relating to chemical synthesis there having been no suggestion that the compound might possess any pharmaceutical properties. The remaining compounds (II) are novel, per se.

Accordingly, the present invention further comprises a compound of formula (II)

wherein $R_1$ and $R_2$ are each separately selected from hydrogen, alkyl, alkenyl and alkynyl groups having up to a maximum of four carbon atoms and being unsubstituted, and alkyl, alkenyl and alkynyl groups having up to a maximum of three carbon atoms and being substituted by one, or in the case of fluoro by one or more, substituents but with the proviso that when $R_1$ is hydrogen then $R_2$ is hydrogen or methyl, or $R_1$ and $R_2$ together constitute an ethylene bridging group, and $R_3$ is a group which under physiological conditions undergoes elimination with the formation of a 3,5-dioxopiperazinyl ring, with the further proviso that when each of $R_1$ and $R_2$ is hydrogen then $R_3$ is not methyl and that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid.

In the single literature report of the preparation of a compound (II) ($R_1=R_2=H$ and $R_3=CH_3$) the copper chelate of the bis cyclic imide (I, $R_1=R_2=H$) is reacted with an excess of methanol and the copper is subsequently removed from the product with hydrogen sulphide. This method works well with methanol but is less successful with ethanol (to give II, $R_1=R_2=H$ and $R_3=C_2H_5$) and becomes progressively more difficult with higher alcohols. We have found that it is advantageous to replace the cupric chloride used by Houghton and Williams to make the initial chelate by a cupric salt of a sulphonic acid such as methane sulphonic or isethionic acid. These give more soluble intermediates which lead to more efficient reactions and, after treatment with hydrogen sulphide, to the direct isolation of more water soluble, pharmaceutically acceptable salt forms of the described products. It may sometimes also be advantageous to add about two equivalents of free sulphonic acid, for example methane sulphonic acid, to the initial reaction mixture. Reasonable yields of diesters from higher alcohols such as 2-butoxyethanol may also be obtained by using an ester exchange reaction between the dimethyl ester, activated in the form of the copper chelate and an excess of the appropriate alcohol. Treatment with hydrogen sulphide may again be used to liberate the desired product. The use of other forms of activated ester for this purpose may also be employed.

A more generally useful method, particularly appropriate where the alcohol is not a liquid, or is uneconomic to use in excess or is pH-labile, is neutral esterification using caesium salts and the appropriate, more reactive, halide as described for simple N-acyl amino acids by Wang et al, (Journal of Organic Chemistry, 1977, 42, 1286). In this procedure the appropriate diacid diamide (prepared as described by Huang et al, Agents and Actions, 1982, 12, 536) is carefully neutralised with caesium bicarbonate (or caesium carbonate) and a solution, or more usually a suspension, of the dried salt in a neutral aprotic solvent such as dimethylformamide, is treated with a reactive halide such as benzyl bromide. The reaction is usually complete within a few hours at from 50° to 100° C. Alternative solvents include hexamethylene phosphoramide, dimethylsulphoxide and N-methylpyrrolidone and the caesium salts can generally be replaced by rubidium salts and, in favourable cases where the halide is particularly reactive such as with the benzyl halides, by salts of other metals including sodium or potassium as well as by salts of tertiary amines such as triethylamine or 4-dimethylaminopyridine.

Yet another procedure involves the use of an acetal of dimethylformamide of formula $(R_3O)_2CH.N(CH_3)_2$ which is reacted with the appropriate diacid diamide, conveniently by heating the two reactants in a suitable mutual solvent, an excess of the acetal generally being employed. Reaction at 50° to 100° C. is usually appropriate, refluxing benzene being suitable as the reaction medium in many cases. This reaction is particularly adapted to the preparation of compounds in which $R_3$ is an unsubstituted alkenyl, alkynyl or particularly alkyl group, for example ethyl, methyl, isopropyl, n-propyl, n-butyl etc.

It will be appreciated that the present invention includes a process for the preparation of a compound of formula (II).

wherein $R_1$ and $R_2$ are each separately selected from hydrogen, alkyl, alkenyl and alkynyl groups having up to a maximum of four carbon atoms and being unsubstituted, and alkyl, alkenyl and alkynyl groups having up to a maximum of three carbon atoms and being substituted by one, or in the case of fluoro by one or more, substituents but with the proviso that when $R_1$ is hydrogen then $R_2$ is hydrogen or methyl, or $R_1$ and $R_2$ together constitute an an ethylene bridging group, and $R_3$ is a group which under physiological conditions undergoes elimination with the formation of a 3,5-dioxopiperazinyl ring, with the further proviso that when each of $R_1$ and $R_2$ is hydrogen then $R_3$ is not methyl and that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, which comprises reacting a compound of formula (III)

or a related compound in which the carboxy groups are in derivature form, including that form in which the carboxy groups are derivatised by the amide groups to form 3,5-dioxopiperazinyl rings, with an alcohol $R_3OH$ or a derivative thereof, where appropriate using a compound of formula (III) or a related compound in the form of a salt with a physiologically acceptable inorganic or organic acid or reacting the compound (II) from the reaction with the alcohol $R_3OH$ or derivative thereof with such an acid to form a salt.

As discussed hereinbefore, the alcohol $R_3OH$ is preferably a primary or secondary one, i.e. the carbon atom joined to the hydroxy group carries one or two hydrogen atoms, in order to produce a compound (II) in which the bonding carbon atom of the group $R_3$ carries at least one hydrogen atom, which would not be the case with a tertiary alcohol. To obtain compounds (II) of the desired stereochemistry it is most convenient to use a compound (III) or a related compound having the equivalent stereochemistry. When a d or l isomer is required rather than the dl isomer, however, an alternative to the utilisation of a d or l compound (III), which is preferred, is to effect a resolution of the compound (II), for example using an appropriate optically active acid to form a mixture of salts of the d and l forms of the compound (II) which are then separated.

The present invention also includes pharmaceutical compositions comprising as an active component a compound of formula (II) as defined hereinbefore, together with a physiologically acceptable diluent or carrier. As indicated, the compounds may be formulated as salts with physiologically acceptable inorganic or organic acids and, when so formulated, it is preferred to use methane sulphonic acid, isethionic acid, tartaric acid or another solubilising acid.

The compounds of formula (II) may be formulated for use as pharmaceuticals by a variety of methods. For instance, they may be applied as aqueous, oily (e.g. as a suspension in isopropyl myristate), or in some cases emulsified compositions for parenteral administration and therefore preferably sterile and pyrogen-free. Some of these compounds have rather low solubility in aqueous media and are therefore usually administered in the form of aqueous suspensions containing suitable surface active agents. It will be appreciated that the dosage levels used may vary over quite a wide range especially since certain of the compounds (I) are more active than others and as the rate of formation of these compounds will depend upon the particular nature of the group $R_3$ in the compound (II) which is being used. Without commitment to a rigid definition of dosages it may be stated that a daily dosage of active constituent (estimated as the free base), divided if necessary, of from 10 mg to 3 g is proposed for mammalian use applied as a solution in 500–1000 ml of liquid for intravenous injection by slow infusion, or as a solution or suspension in about 10 ml of liquid by the intramuscular route, or in small volumes subcutaneously. More particularly, by way of example, when the active compound (II) has a group $R_1$ which is hydrogen or methyl and a group $R_2$ which is hydrogen the daily dose for a 70 kg human, administered parenterally will often be in the range from 100 mg to 500 mg but with the more active compounds in which $R_1$ is methyl and $R_2$ is methyl or ethyl it will tend to be less than this (the dose being varied pro rata for humans of a different weight or other mammals).

The substances may also be compounded for oral administration in dosages which may be similar but may often be somewhat higher, for example in a range from 100 mg to 1 g or even as high as 3 g for the daily dose for a 70 kg human when $R_1 = H$ or $CH_3$ and $R_2 = H$ but often somewhat less than this when $R = CH_3$ and $R_2 = CH_3$ or $C_2H_5$. Such oral formulations may particularly take the form of tablets compounded in the presence of conventional solid carrier materials such as starch, lactose, dextrin and magnesium stearate, or of capsules, aerosols or cachets. For the treatment of local forms of the disease, compositions adapted for topical application may be used, for example suitable creams or drops may be prepared containing the active substance or an aerosol formulation. Suppositories, pessaries and other formulations may also be employed. The compounds may be formulated in unit dosage form, i.e. in discrete portions each containing a unit does, or a multiple or sub-multiple of a unit dose of the active ingredient.

It will be appreciated that certain formulations of the compounds (II) will tend to cyclise to the compounds (I) on storage if made up in advance. For this reason, although the compounds may conveniently be formulated in advance of their use as a solid composition it will usually be appropriate to prepare certain forms of liquid composition, particularly those containing an aqueous diluent, just prior to their use. Providing such steps are taken to avoid premature cyclisation before administration, however, it will be appreciated from the foregoing discussion that the compounds used may have a very wide range of half lives in vivo.

The compounds are of value in the treatment of psoriasis and of certain forms of inflammatory activity, particularly inflammatory conditions of the eye such as uveitis, but also inflammatory bowel disease. They are applicable primarily in the treatment of humans and although they can find veterinary use in certain other mammals such as dogs, rabbits, cattle, and horses, their activity is not expressed in rodents such as rats and mice owing to an esterase activity existing in the plasma thereof which prevents cyclisation of the compounds (II) to the compounds (I).

If desired, a mixture of two or more compounds (II) may be employed in the present invention. Moreover, it is also possible to use the compounds (II) in combination with other compounds. In particular, they can be precombined advantageously with anthracycline drugs such as doxorubicin and provide a protective effect against the cardiotoxicity of these agents.

The invention is illustrated by the following Examples.

EXAMPLE 1

A mixture of 1,2-bis-(3,5-dioxopiperazin-1-yl)ethane (25.4 g, 0.1 moles) (prepared as described in UK Patent Specification No. 1,234,935), cupric methanesulphonate (25.4 g, 0.1 moles) (prepared from equivalent amounts of cupric acetate and methanesulphonic acid) and dry methanol (500 ml) was stirred and heated together under reflux for 48 hours. The reaction mixture was then evaporated to dryness and the residue taken up in water (200 ml), saturated with hydrogen sulphide and then filtered. The colourless solution was evaporated to dryness to yield a white solid which was recrystallised from methanol (100 ml containing a little water to give, on cooling, 25.5 g of the methyl diester. Concentration of the mother liquors to 50 ml followed by dilution with acetone (50 ml) gave on cooling a further 7.0 g yielding a total of 32.5 g (62%) of NN'-Dimethoxycarbonylmethyl-NN'-diaminocarbonylmethyl-1,2-diaminoethane dimethanesulphonate monohydrate. Both crops had m.p. 189°–190° (dec). Treatment of a sample suspended in chloroform with dry ammonia gave the base, m.p. 140°–142° C. from methanol.

Similarly prepared from the appropriate alcohols and bis-imides were:

dl-NN'-Dimethoxycarbonylmethyl-NN'-diaminocarbonylmethyl-1,2-diaminopropane, as the free base in 15% yield (after conversion from the dimethanesulphonate), m.p. 107°–108° from n-propanol/cyclohexane.

NN'-Diethoxycarbonylmethyl-NN'-diaminocarbonylmethyl-1,2-diaminoethane dimethanesulphonate monohydrate, (60% yield) m.p. 186°–187° (dec) from aqueous ethanol. The free base has m.p. 138°–139° from ethanol.

NN'-Di-isobutoxycarbonylmethyl-NN'-diaminocarbonylmethyl-1,2-diaminoethane dimethanesulphonate (42% yield), m.p. 187° C. (dec) from aqueous acetone.

NN'-Di-(2-methoxyethoxy)carbonylmethyl-NN'-diaminocarbonylmethyl-1,2-diaminoethane, as the free base in 36% yield (after conversion from the dimethanesulphonate), m.p. 120°–123° from ethanol.

NN'-Di-isopropoxycarbonylmethyl-NN'-diaminocarbonylmethyl-1,2-diaminoethane, as the free base in 37% yield, m.p. 188°–189° C. from ethanol. (Two equivalents of p-toluensulphonic acid were added to help increase the solubility of the reactants and consequently the product initially isolated was a mixture of methanesulphonate and toluenesulphonate salts).

NN'-Di-(2-hydroxyethoxy)carbonylmethyl-NN'-diaminocarbonylmethyl-1,2-diaminoethane dimethanesulphonate monohydrate, (16% yield, m.p. 175°–176° C. (dec) from isopropanol.

NN'-Di-(2-n-butoxyethoxy)carbonylmethyl-NN'-diaminocarbonylmethyl-1,2-diaminoethane, as the free base in 4% yield, m.p. 99°–100° C. (dec) from isopropanol.

EXAMPLE 2

An aqueous solution of caesium carbonate (16 ml, 20%, 10 mmoles was added dropwise to a stirred suspension of dl-NN'-dicarboxymethyl-NN'-diaminocarbonylmethyl-1,2-diaminopropane monohydrate (prepared as described by Huang et al, Agents and Actions, 1982, 12, 536) (3.22 g, 10 mmoles) in methanol (40 ml) and water (10 ml) at below −5° C. The clear solution was then evaporated to dryness at or below 20° C. The dried solid residue was suspended in dimethyl formamide (80 ml) and stirred overnight at room temperature with propargyl bromide (1.7 ml, 22 mmoles). The temperature was raised over half an hour up to 80° C. and the caked solid broken up as far as possible with a spatula. Heating was continued for 1½ hours and the reaction mixture then evaporated to dryness and partitioned between water and methylene chloride. Concentration of the methylene chloride layer gave an oil which crystallised from isopropanol to give 2.1 g of the crude propargyl diester. Recrystallisation from isopropanol containing a very little methanol gave dl-NN'-Dipropargyloxycarbonylmethyl-NN'-diaminocarbonylmethyl-1,2-diaminopropane, 1.76 g (46%), m.p. 99°–101° C.

Similarly prepared from the appropriate halides and bis acid/amides were:

dl-NN'-Dibenzyloxycarbonylmethyl-NN'-diaminocarbonylmethyl-1,2-diaminopropane, prepared from benzyl bromide in 34% yield, m.p. 92°–93° C. from methanol/isopropanol.

dl-NN'-Di-p-nitrobenzyloxycarbonylmethyl-NN'-diaminocarbonylmethyl-1,2-diaminopropane, prepared from p-nitrobenzylbromide in 53% yield, m.p. 153°–154° C. from methanol.

EXAMPLE 3

A suspension of $CsHCO_3$ (1.94 g, 10 mmoles) in methanol (25 ml) was added slowly to a stirred suspension of dl-NN'-dicarboxymethyl-NN'-diaminocarbonylmethyl-1,2-diaminopropane monohydrate (1.61 g, 5 mmoles) in methanol at −20° C. and the mixture allowed to warm up to 10° C. during an hour when complete solution was achieved. The solution was evaporated to dryness and the residue suspended in dimethylformamide (50 ml) and treated with phenacyl bromide (2.19 g, 11 mmoles). The reaction mixture was heated with stirring up to 70° C. over an hour, at 70° C. for 2 hours and then at 100° C. for 2 hours and then evaporated to dryness. The residue was triturated with chloroform, filtered from caesium bromide (1.8 g) and the filtrate evaporated to an oil which crystallised from isopropanol to give, after recrystallation, 1.54 g (54%) of dl-NN'-Diphenacyloxycarbonylmethyl-NN'-diaminocarbonylmethyl-1,2-diaminopropane, as a dihydrate, m.p. 80°–81° C.

Similarly prepared from the appropriate halides and bis acid/amides were:

dl-NN'-Di-(2,6-dichlorobenzyloxycarbonylmethyl)-NN'-diaminocarbonylmethyl-1,2-diaminopropane, prepared from 2,6-dichlorobenzyl bromide in 69% yield, m.p. 157°–158° C. from dimethylformamide/methanol.

dl-NN'-Di-o-nitrobenzyloxycarbonylmethyl)-NN'-diaminocarbonylmethyl-1,2-diaminopropane, prepared from o-nitrobenzyl bromide in 44% yield, m.p. 135°–136° C. from methanol.

EXAMPLE 4

The following compounds were prepared according to the general procedure of Example 2 except that an equivalent amount of caesium bicarbonate rather than caesium carbonate was used to prepare the initial caesium salts:

NN'-Dibenzyloxycarbonylmethyl-NN'-diaminocarbonylmethyl-1,2-diaminoethane, prepared from benzyl bromide in 27% yield, m.p. 169°–170° C.

NN'-Diphenacyloxycarbonylmethyl-NN'-diaminocarbonylmethyl-1,2-diaminoethane, prepared from phenacyl bromide in 83% yield, m.p. 200°–203° C. from methanol.

NN'-Di-p-nitrobenzyloxycarbonylmethyl-NN'-diaminocarbonylmethyl-1,2-diaminoethane, prepared from p-nitrobenzyl bromide in 64% yield, m.p. 195°–196° C. from dimethylformamide.

NN'-Di-(2,6-dichlorobenzyloxycarbonylmethyl)-NN'-diaminocarbonylmethyl-1,2-diaminoethane, prepared from 2,6-dichlorobenzyl bromide in 80% yield, m.p. 202°–203° C. from dimethylformamide/methanol.

NN'-Di-(6-chloropiperonyloxycarbonylmethyl)-NN'-diaminocarbonylmethyl-1,2-diaminoethane, prepared from 6-chloropiperonyl bromide in 14% yield, m.p. 165°–168° C. from dimethylformamide.

NN'-Di-(ethoxycarbonylmethyloxycarbonylmethyl)-NN'-diaminocarbonylmethyl-1,2-diaminoethane, prepared from ethyl chloroacetate in 78% yield, m.p. 142°–143° C. from methanol.

NN'-Di-(3-ethoxycarbonylpropyloxycarbonylmethyl)-NN'-diaminocarbonylmethyl-1,2-diaminoethane, prepared from ethyl-4-bromobutyrate in 37% yield m.p. 195° C. from dimethylformamide.

NN'-Di-(benzyloxycarbonylmethyloxycarbonylmethyl)-NN'-diaminocarbonylmethyl-1,2-diaminoethane, prepared from benzyl bromoacetate in 57% yield, m.p. 127°–128° C. from methanol.

NN'-Di-(t-butoxycarbonylmethyloxycarbonylmethyl)-NN'-diaminocarbonylmethyl-1,2-diaminoethane, prepared from t-butyl bromoacetate in 29% yield, m.p. 105°–107° C. from methanol/isopropanol.

NN'-Di-(1-phenyloxycarbonylethyl)-NN'-diaminocarbonylmethyl-1,2-diaminoethane, prepared from α-methylbenzyl bromide in 6% yield, m.p. 138°–141° C. from methanol.

NN'-Di(diethoxycarbonylmethyloxycarbonylmethyl)-NN'-diaminocarbonylmethyl-1,2-diaminoethane, prepared from diethyl α-bromomalonate in 8% yield, m.p. 78°–79° C. from ethanol.

meso-NN'-Di-(benzyloxycarbonylmethoxyloxycarbonylmethyl)-NN'-diaminocarbonylmethyl-2,3-diaminobutane, prepared from benzyl bromoacetate in 67% yield, m.p. 152°–153° C. from methanol.

NN'-Di-(propargyloxycarbonylmethyl)-NN'-diaminocarbonymethyl-1,2-diaminoethane, prepared from propargyl bromide in 31% yield, m.p. 127°–128° C. from isopropanol.

NN'-Di-(cyanomethylcarbonylmethyl-NN'-diaminocarbonylmethyl-1,2-diaminoethane, prepared from chloroacetonitrile in 10% yield.

EXAMPLE 5

NN'-Di-(benzyloxycarbonylmethyloxycarbonylmethyl)-NN'-diaminocarbonylmethyl-1,2-diaminoethane (7.0 g, 11.9 mmoles) in dimethylformamide (200 ml) was hydrogenated over a palladium/charcoal catalyst (0.7 g) at about 40° C. to maintain solution. After ½ hour the reaction appeared complete (TLC) and the catalyst was removed by filtration. Concentration and crystallisation gave NN'-Di-(carboxymethyloxycarbonylmethyl)-NN'-diaminocarbonylmethyl-1,2-diamonoethane, 4.5 g (93%), m.p. 180°–181° C. from dimethyl formamide/ethanol.

Similarly prepared from the corresponding dibenzyl ester was: meso-NN'-Di-(carboxymethyloxycarbonylmethyl)-NN'-diaminocarbonylmethyl-2,3-diaminobutane, in near quantitative yield, m.p. 210°–211° C. from dimethylformamide/ethanol/acetone.

EXAMPLE 6

NN-Dimethylformamide diethylacetal (16.2 g, 80 mmoles; Pierce Chemical Company) was added dropwise during 10 minutes to a stirred suspension of NN'-dicarboxymethyl-NN'-diaminocarbonylmethyl-1,2-diaminoethane (2.9 g, 10 mmoles) in dimethylformamide (75 ml) at 100° C. After a further 30 minutes at 100° C., the solvent was evaporated off under reduced pressure and the residue crystallised from isopropanol. Further recrystallisation from ethanol gave NN'-diethoxycarbonylmethyl-NN'-diaminocarbonylmethyl-1,2-diaminoethane, m.p. 130°–140° C.

EXAMPLE 7

A mixture of 1,2-bis(3,5-dioxopiperazin-1-yl)ethane (25.4 g, 0.1 moles) and cupric methane sulphate (25.4 g, 0.1 moles) in dry methanol (500 ml) was heated under reflux for 48 hours. The methanol was removed by evaporation under reduced pressure and replaced by 2-n-butoxyethanol (500 ml) and the resultant solution heated under nitrogen for 10 hours at 120° C. The solvent was removed by evaporation under reduced pressure and the residue taken up in warm acetic acid (300 ml) and water (100 ml). The solution was then saturated with $H_2S$, filtered through Keiselguhr and the filtrate evaporated to a low bulk. The residue was dissolved in water (100 ml), and crushed ice (100 g) and an excess of sodium acetate were added and the mixture extracted several times with chloroform. The microcrystalline material obtained on evaporation was purified by passing 0.5 g batches through a Zorbax ODS HPLC column (2.5 cm × 28 cm) using gradient elution with methanol/water and a 3 ml injection loop. The product was crystallised from isopropanol to give NN'-Di-(2-n-butoxyethoxy)carbonylmethyl-NN'-diaminocarbonylmethyl-1,2-diaminoethane, 14.6 g (32%), m.p. 99°–100° C. (dec).

EXAMPLE 8

Tablets of the following composition are prepared:

|  | mg/tablet |
| --- | --- |
| Compound of Example 2 (micronised) | 250 |
| 'Avicel' (microcrystalline cellulose) | 38 |
| polyvinylpyrrolidone | 3 |
| alginic acid | 6 |
| magnesium sterate | 3 |

Any one of the products prepared in Example 2 is mixed with 'Avicel' and polyvinylpyrrolidone is added, dissolved in sufficient industrial methylated spirits (74° OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium sterate are then added and mixed with the granules. The product is compressed into tablets each weighting 300 mg on ⅜ inch flat bevelled edge divided punches.

EXAMPLE 9

Tablets of the following composition are prepared:

|  | mg/tablet |
| --- | --- |
| Compound of Example 2 (micronised) | 250 |
| 'Avicel' (microcrystalline cellulose) | 134 |
| polyvinylpyrrolidone | 4 |
| alginic acid | 8 |
| magnesium sterate | 4 |

The tablest are prepared by essentially the same procedure as described in Example 6, using any one of the products prepared in Example 2, and are compressed at a tablet weight of 400 mg on 7/16 inch flat bevelled edge punches.

EXAMPLE 10

Tablets of the following composition are prepared:

|  | mg/tablet |
| --- | --- |
| Compound of Example 2 (micronised) | 250 |
| lactose (300 mesh) | 19 |
| maize starch | 15 |
| gelatine | 10 |
| magnesium sterate | 6 |

The tablets are prepared by mixing any one of the products prepared in Example 2 with lactose and half the total quantity of maize starch required, and adding to the mass a 5% solution of gelatine in water. The product is granulated through a 16 mesh sieve, and the resultant granules are dried to constant weight at a temperature not exceeding 50° C. The dried granules are passed through a 20 mesh sieve and mixed with magnesium stearate and the remained of the maize starch. The product is compressed at a 300 mg tablet weight on ⅜ inch flat bevelled edge divided punches.

EXAMPLE 11

(A) The cytotoxic effects of a variety of compounds of formula (II) on human adenocarcinoma cells of the colon (LOVO) and human mammary epithelial tumor cells (MCF7) grown in culture were studied. A range of doses of the drugs was added on day one to replicate cultures of several hundred cells each, which were then incubated at 37° C. for 12-14 days. The cultures were then fixed and stained and the numbers of colonies per dish counted. The results obtained are shown in Table 1, the individual compounds being identified by the groups $R_1$, $R_2$ and $R_3$ present therein, the last mentioned compound being the compound of formula (I) having $R_1=H$ and $R_2=CH_3$ which is used as a control. The results are expressed in terms of the $ID_{50}$ which is the dose required to reduce by 50% the number of colonies growing up in the drug-treated cultures compared with untreated controls.

TABLE 1

| Compound | | | $ID_{50}$ ($\mu M$) | |
| --- | --- | --- | --- | --- |
| $R_1$ | $R_2$ | $R_3$ | LOVO | MCF7 |
| H | H | $CH_3$ | 28 | 39 |
| H | H | $CH_2CH(CH_3)_2$ | 103 | 121 |
| $CH_3$ | H | $CH_2C_6H_5$ | 17 | 22 |
| H | H | $CH_2CH_2O(CH_2)_3CH_3$ | 47 | 36 |
| $CH_3$ | H | p-$NO_2$—$CH_2C_6H_5$ | 14 | 21 |
| H | H | $CH_2CO_2H$ | 67 | 46 |
| $CH_3$ | H | o-$NO_2$—$CH_2C_6H_5$ | 11 | 16 |
| $CH_3$ | $CH_3$ | $CH_2CO_2H$ | 0.2 | 1.1 |
| H | H | $CH(CH_3)C_6H_5$ | 35 | 31 |
| H | H | $CH(CO_2C_2H_5)_2$ | 18 | 25 |
| $CH_3$ | H | cyclic imide | 18 | 17 |

(B) The rate of formation of the active antitumor agent (I) having $R_1=$ and $R_2=H$ from the corresponding $^{14}C$-labelled dimethyl ester (II) ($R_1=R_2=H$, $R_3=CH_3$) following incubation under physiologically conditions, i.e. at 37° C. and pH and 7.2 in normal (0.15M) phosphate buffered saline [Practical Immunology, Hudson and hay (editors), Blackwell Scientific Publications, Second Edition, 1980, page 336] was studied. Sample of the incubation mixture were fractionated at different time intervals using HPLC with a reverse phase ODS column and an aqueous methanol gradient elution system. The results are shown in the Figure from which it will be seen that although the diimide itself hydrolyses to an inactive form, having a half life of about 12 hours at pH 7.2, its slow formation by cyclisation of the bis-ester, via the ester amide/imide compound containing one ring, leads to a sustained concentration of the active cytotoxic species.

We claim:

1. A pharmaceutical composition suitable for effecting cardioprotection, comprising an effective amount of a compound of formula (II)

wherein $R_1$ and $R_2$ are each separately selected from the group consisting of hydrogen, alkyl, alkenyl and alkynyl groups having up to a maximum of four carbon atoms and being unsubstituted, and alkyl, alkenyl and alkynyl groups having up to a maximum of three carbon atoms and being substituted by one phenyl, carboxy, alkoxycarbonyl, halogeno (other than fluoro), hydroxy or alkoxy group, or by one or more fluoro groups, but with the proviso that when $R_1$ is hydrogen then $R_2$ is hydrogen or methyl, or $R_1$ and $R_2$ together constitute an ethylene bridging group, and $R_3$ excludes and group in which the bonding carbon atoms does not carry at least one hydrogen atom, $R_3$ being selected from the group consisting of (a) alkyl, alkenyl and alkynyl groups having up to a maximum of ten carbon atoms and being either unsubstituted or substituted by one or more alkoxy, carboxy, halogeno, hydroxy, alkoxycarbonyl, benzyloxycarbonyl, cyano, amino, alkylamino, dialkyamino or oxo groups and (b) aralkyl, aralkenyl and aralkynyl groups in which the aromatic part of the group may optionally be substituted by one or two substituents selected from the group consisting of halogeno, lower alkyl, lower alkoxy, amino and nitro groups or by one methylenedioxy group, and in which the aliphatic part of the group has up to a maximum of ten carbon atoms and may optionally be substituted by one substituent selected from the group consisting of alkoxycarbonyl and cyano groups, with the further proviso that when each of $R_1$ and $R_2$ is hydrogen then $R_3$ is not methyl and that the compound is in the meso or erythro configuration when each $R_1$ and $R_2$ is the same or different unsubstituted or substituted alkyl, alkenyl or alkynyl group, and salts thereof with a physiologically acceptable inorganic or organic acid, together with a physiologically acceptable diluent or carrier.

2. A pharmaceutical composition according to claim 1 in which the aromatic part of the aralkyl, aralkenyl an aralkynyl group $R_3$ is an unsubstituted or substituted phenyl group.

3. A pharmaceutical composition according to claim 1 in which the group $R_3$ excludes any unsubstituted or substituted alkyl, alkenyl or alkynyl group in which the bonding carbon atom is either unsaturated or is linked to an atom which is not hydrogen or carbon.

4. A pharmaceutical composition according to claim 1 in which $R_3$ is selected from the group consisting of unsubstituted alkyl, alkenyl and alkynyl groups and substituted alkyl groups as defined under (a) having one or, in the case of alkoxycarbonyl groups, one or two substituents.

5. A pharmaceutical composition according to claim 1 in which $R_3$ is selected from the group consisting of substituted benzyl groups as defined therein 6. A pharmaceutical composition according to claim 1 in which the substituted alkyl, alkenyl and alkynyl groups from which $R_1$ and $R_2$ are substituted by one halogeno (other than fluoro), hydroxy or alkoxy group or by one or more fluoro groups.

7. A pharmaceutical composition according to claim 1 in which $R_1$ and $R_2$ are each separately selected from the group consisting of hydrogen and unsubstituted alkyl, alkenyl and alkynyl groups, or $R_1$ and $R_2$ together represent an ethylene bridging group.

8. A pharmaceutical composition according to claim 1 in which the compound is in the form of a salt with methane sulphonic acid, isethionic acid or tartaric acid.

9. A pharmaceutical composition according to claim 1 in which $R_3$ is selected from the group consisting of alkyl, alkenyl and alkynyl and alkoxyalkyl groups having up to a maximum of ten carbon atoms.

10. A pharmaceutical composition according to claim 1 in which $R_3$ is an aralkyl group in which the aromatic part of the group may optionally by substituted by one or two substituents selected from the group consisting of halogen, lower alkyl, lower alkoxy, amino and nitro groups or by one methylenedioxy group, and in which the alkyl part of the group has a maximum of ten carbon atoms and may be substituted by an alkoxycarbonyl or cyano group.

11. A pharmaceutical composition according to claim 1 in which the aralkyl group is a phenylalkyl group which may optionally be substituted as described in claim 10.

12. A pharmaceutical composition according to claim 1 in which $R_3$ is a halogenoalkyl, hydroxyalkyl, alkoxycarbonylalkyl, di-(alkoxycarbonyl)-alkyl, benzyloxycarbonylalkyl, cyanoalkyl, aminoalkyl or di-(alkylamino)-alkyl group, with the alkyl part in any group containing not more than ten carbon atoms.

13. A pharmaceutical composition suitable for effecting cardioprotection, comprising an effective amount of formula (II).

wherein $R_1$ and $R_2$ are each separately selected from the group consisting of hydrogen and unsubstituted alkyl, alkenyl and alkynyl groups having up to a maximum for four carbon atoms, but with the proviso that when $R_1$ is hydrogen then $R_2$ is hydrogen or methyl, or $R_1$ and $R_2$ together constitute an ethylene bridging group, and $R_3$ is selected from the group consisting of methyl, ethyl, n-propyl, n-butyl, isobutyl, allyl, propargyl, benzyl, α-methylbenzyl, α-ethoxycarbonylbenzyl, nitrobenzyl, aminobenzyl, chlorobenzyl, dichlorobenzyl, chloro-3,4-methylenedioxybenzyl, methoxybenzyl, dimethoxybenzyl, methylbenzyl, dimethylbenzyl, cinnamyl, methoxyethyl, ethoxyethyl, propoxyethyl, butoxyethyl, hydroxyethyl, hydroxypropyl, hydroxybutyl, ethoxycarbonylmethyl, ethoxycarbonylethyl, ethoxycarbonylpropyl, carboxymethyl, carboxyethyl, carboxypropyl, benzyloxycarbonylmethyl, benzyloxycarbonylethyl, benzyloxycarbonylpropyl, t-butoxycarbonylmethyl, t-butoxycarbonylethyl, t-butoxycarbonylpropyl, di-(ethoxycarbonyl) methyl, cyanomethyl, acetonyl, phenacyl, and 3-dimethylaminopropyl groups with the proviso that the bonding carbon atom of each group $R_3$ is linked only to atoms which are hydrogen or carbon and with the further proviso that when each of $R_1$ and $R_2$ is hydrogen then $R_3$ is not methyl and that the compound is in the meso or erythro configuration when each of $R_1$ and $R_2$ is the same or different unsubstituted alkyl, alkenyl or alkynyl group, and salts thereof with a physiologically acceptable inorganic or organic acid, together with a physiologically acceptable diluent or carrier.

14. A pharmaceutical composition according to claim 13 in which $R_1$ and $R_2$ are each hydrogen, $R_1$ is methyl and $R_2$ is hydrogen, methyl, ethyl, n-propyl, isopropyl, allyl or propargyl, $R_1$ and $R_2$ are each separately selected from the group consisting of ethyl, n-propyl, isopropyl, allyl and propargyl, or $R_1$ and $R_2$ together represent an ethylene bridging group.

15. A pharmaceutical composition according to claim 13 in which $R_1$ and $R_2$ are each hydrogen, $R_1$ is methyl and $R_2$ is hydrogen, methyl or ethyl, $R_1$ and $R_2$ are each ethyl, or $R_1$ and $R_2$ together represent an ethylene bridging group, and $R_3$ is selected from the group consisting of methyl, isobutyl, allyl, propargyl, benzyl, α-methylbenzyl, α-carbethoxybenzyl, o-nitrobenzyl, aminobenzyl, 2,6-dichlorobenzyl, methoxyethyl, ethoxyethyl, propoxyethyl, butoxyethyl, hydroxyethyl, hydroxypropyl, hydroxybutyl, ethoxycarbonylmethyl, di-(ethoxycarbonyl)-methyl, benzyloxycarbonylmethyl, ethoxycarbonylpropyl, carboxymethyl and acetonyl, with the proviso that the bonding carbon atom of each group $R_3$ is linked only to atoms which are hydrogen or carbon.

16. A pharmaceutical composition according to claim 13 in which $R_1$ and $R_2$ are each hydrogen.

17. A pharmaceutical composition according to claim 13 in which $R_1$ is methyl and $R_2$ is hydrogen.

18. A pharmaceutical composition according to claim 13 in which $R_1$ and $R_2$ together represent an ethylene bridging group.

19. A pharmaceutical composition according to claim 13 in which $R_3$ is acetonyl or phenacyl.

20. A pharmaceutical composition according to claim 5 in which $R_3$ is propargyl.

21. A pharmaceutical composition according to claim 13 in which the compound is dl-NN'-dipropargyloxycarbonylmethyl-NN'-diaminocarbonyl-methyl-1,2-diaminopropane, and salts thereof with a physiologically acceptable inorganic or organic acid.

22. A pharmaceutical composition according to claim 13 in which $R_1$ is methyl, $R_2$ is hydrogen and $R_3$ is selected from the group consisting of methyl, ethyl, isobutyl, allyl, propargyl, benzyl, α-methylbenzyl, α-ethoxycarbonylbenzyl, o-nitrobenzyl, aminobenzyl, 2,6-dichlorobenzyl, methoxyethyl, ethoxyethyl, propoxyethyl, butoxyethyl, hydroxyethyl, hydroxypropyl, hydroxybutyl, ethoxycarbonylmethyl, di-(ethoxycarbonyl)-methyl, benzyloxycarbonylmethyl, ethoxycarbonylpropyl, carboxymethyl and acetonyl, with the proviso that the bonding carbon atom of each group $R_3$ is linked only to atoms which are hydrogen or carbon.

23. A pharmaceutical composition according to claim 13 in which $R_1$ and $R_2$ are each hydrogen and $R_3$ is selected from the group consisting of methyl, ethyl, isobutyl, allyl, propargyl, benzyl, α-methylbenzyl, α-ethoxycarbonylbenzyl, o-nitrobenzyl, aminobenzyl, 2,6-dichlorobenzyl, methoxyethyl, ethoxyethyl, propoxyethyl, butoxyethyl, hydroxyethyl, hydroxypropyl, hydroxybutyl, ethoxycarbonylmethyl, di-(ethoxycarbonyl)-methyl, benzyloxycarbonylmethyl, ethoxycarbonylpropyl, carboxymethyl and acetonyl, with the proviso that the bonding carbon atom of each group $R_3$ is linked only to atoms which are hydrogen or carbon.

24. A pharmaceutical composition according to claim 13 in which $R_1$ and $R_2$ together represent an ethylene bridging group and $R_3$ is selected from the group consisting of methyl, ethyl, isobutyl, allyl, propargyl, benzyl, α-methylbenzyl, α-ethoxycarbonylbenzyl, o-nitrobenzyl, aminobenzyl, 2,6-dichlorobenzyl, methoxyethyl, ethoxyethyl, propoxyethyl, butoxyethyl, hydroxyethyl, hydroxypropyl, hydroxybutyl, ethoxycarbonylmethyl, di-(ethoxycarbonyl)-methyl, benzyloxycarbonylmethyl, ethoxycarbonylpropyl, carboxymethyl and acetonyl, with the proviso that the bonding carbon atom of each group $R_3$ is linked only to atoms which are hydrogen or carbon.

25. A pharmaceutical composition suitable for effecting cardioprotection, said composition comprising an effective amount of a compound of formula (II)

wherein $R_1$ and $R_2$ are each separately selected from the group consisting of hydrogen, alkyl, alkenyl and alkynyl groups having up to a maximum of four carbon atoms and being unsubstituted, and alkyl, alkenyl and alkynyl groups having up to a maximum of three carbon atoms and being substituted by one phenyl, carboxy, alkoxycarbonyl, halogeno (other than fluoro), hydroxy or alkoxy group, or by one or more fluoro groups, but with the proviso that when $R_1$ is hydrogen then $R_2$ is hydrogen or methyl, or $R_1$ and $R_2$ together constitute an ethylene bridging group, and $R_3$ excludes any group in which the bonding carbon atoms does not carry at least one hydrogen atom, $R_3$ being selected from the group consisting of (a) alkyl, alkenyl and alkynyl groups having up to a maximum of ten carbon atoms and being either unsubstituted or substituted by one or more alkoxy, carboxy, halogeno, hydroxy, alkoxycarbonyl, benzyloxycarbonyl, cyano, amino, alkylamino, dialkyamino or oxo groups and (b) aralkyl, aralkenyl and aralkynyl groups in which the aromatic part of the group may optionally be substituted by one or two substituents selected from the group consisting of halogeno, lower alkyl, lower alkoxy, amino and nitro groups or by one methylenedioxy group, and in which the aliphatic part of the group has up to a maximum of ten carbon atoms and may optionally be substituted by one substituent selected from the group consisting of alkoxycarbonyl and cyano groups, with the further proviso that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, together with a physiologically acceptable diluent or carrier which is sterile and pyrogen-free.

26. A pharmaceutical composition suitable for effecting cardioprotection, said composition comprising an effective amount of a compound of formula (II)

wherein $R_1$ and $R_2$ are each separately selected from the group consisting of hydrogen, alkyl, alkenyl and alkynyl groups having up to a maximum of four carbon atoms and being unsubstituted, and alkyl, alkenyl and alkynyl groups having up to a maximum of three carbon atoms and being substituted by one phenyl, carboxy, alkoxycarbonyl, halogeno (other than fluoro), hydroxy or alkoxy group, or by one or more fluoro groups, but with the proviso that when $R_1$ is hydrogen then $R_2$ is hydrogen or methyl, or $R_1$ and $R_2$ together constitute an ethylene bridging group, and $R_3$ excludes any group in which the bonding carbon atoms dose not carry at least one hydrogen atom, $R_3$ being selected from the group consisting of (a) alkyl, alkenyl and alkynyl groups having up to a maximum of ten carbon atoms and being either unsubstituted or substituted by one or more alkoxy, carboxy, halogeno, hydroxy, alkoxycarbonyl, benzyloxycarbonyl, cyano, amino, alkylamino, dialkyamino or oxo groups and (b) aralkyl, aralkenyl and aralkynyl groups in which the aromatic part of the group may optionally be substituted by one or two substituents selected from the group consisting of halogeno, lower alkyl, lower alkoxy, amino and nitro groups or by one methylenedioxy group, and in which the aliphatic part of the group has up to a maximum of ten carbon atoms and may optionally be substituted by one substituent selected from the group consisting of alkoxycarbonyl and cyano groups, with the further proviso that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, together with a physiologically acceptable solid carrier.

27. A pharmaceutical composition according to claim 26 adapted for oral administration.

28. A method for the treatment of inflammatory disease, which method comprises the step of administering to a patient in need thereof a therapeutically effective amount of a compound of formula (II)

(II)

wherein $R_1$ and $R_2$ are each separately selected from the group consisting of hydrogen, alkyl, alkenyl and alkynyl groups having up to a maximum of four carbon atoms and being unsubstituted, and alkyl, alkenyl and alkynyl groups having up to a maximum of three carbon atoms and being substituted by one phenyl, carboxy, alkoxycarbonyl, halogeno (other than fluoro), hydroxy or alkoxy group, or by one or more fluoro groups, but with the proviso that when $R_1$ is hydrogen then $R_2$ is hydrogen or methyl, or $R_1$ and $R_2$ together constitute an ethylene bridging group, and $R_3$ excludes any group in which the bonding carbon atoms does not carry at least one hydrogen atom, $R_3$ being selected from the group consisting of (a) alkyl, alkenyl and alkynyl groups having up to a maximum of ten carbon atoms and being either unsubstituted or substituted by one or more alkoxy, carboxy, halogeno, hydroxy, alkoxycarbonyl, benzyloxycarbonyl, cyano, amino, alkylamino, dialkyamino or oxo groups and (b) aralkyl, aralkenyl and aralkynyl groups in which the aromatic part of the group may optionally be substituted by one or two substituents selected from the group consisting of halogeno, lower alkyl, lower alkoxy, amino and nitro groups or by one methylenedioxy group, and in which the aliphatic part of the group has up to a maximum of ten carbon atoms and may optionally be substituted by one substituent selected from the group consisting of alkoxycarbonyl and cyano groups, with the further proviso that the compound is in the meso or erythro configuration when each of $R_1$ and $R_2$ is the same or different unsubstituted or substituted alkyl, alkenyl or alkynyl group, and salts thereof with a physiologically acceptable inorganic or organic acid, together with a physiologically acceptable diluent or carrier.

* * * * *